(12) United States Patent
Hermeking

(10) Patent No.: US 6,221,106 B1
(45) Date of Patent: Apr. 24, 2001

(54) DIAPHRAGM FOR IMPLANTATION IN THE LENS CAPSULE SAC OF AN EYE

(76) Inventor: Heino Hermeking, Falkenberg 137, D-42113 Wuppertal (DE)

( * ) Notice: Subject to any disclaimer, the term of this patent is extended or adjusted under 35 U.S.C. 154(b) by 0 days.

(21) Appl. No.: 09/247,630

(22) Filed: Feb. 10, 1999

(30) Foreign Application Priority Data

Jun. 11, 1997 (DE) .............................. 197 24 539

(51) Int. Cl.[7] .................................................. A61F 2/16
(52) U.S. Cl. .......................................... 623/6.4; 623/6.43
(58) Field of Search .................. 623/6, 6.11, 6.38–6.43, 623/6.51; 606/1, 151, 166

(56) References Cited

U.S. PATENT DOCUMENTS

| | | | |
|---|---|---|---|
| 4,782,820 | * 11/1988 | Woods | 128/20 |
| 4,961,744 | * 10/1990 | Kilmer et al. | 606/166 |
| 5,133,750 | * 7/1992 | Momose et al. | 623/6 |
| 5,275,624 | * 1/1994 | Hara et al. | 623/6 |
| 5,505,722 | * 4/1996 | Kilmer et al. | 606/1 |
| 5,628,797 | 5/1997 | Richer . | |
| 6,083,261 | * 7/2000 | Callahan et al. | 623/6.38 |

FOREIGN PATENT DOCUMENTS

| | | | |
|---|---|---|---|
| 39 265 36 | 2/1991 | (DE) . | |
| 0319154 | 11/1988 | (EP) . | |
| 0 366 390 | * 11/1989 | (EP) | 623/6 |
| 2696340 | 1/1993 | (FR) . | |
| PCT/US95/04774 | 4/1995 | (WO) . | |

* cited by examiner

*Primary Examiner*—David H. Willse
*Assistant Examiner*—Suzette J. Jackson
(74) *Attorney, Agent, or Firm*—Galgano & Burke

(57) ABSTRACT

The diaphragm (10, 12) for creating an artificial pupil aperture is functionally decoupled from a capsule bracing ring. Together with an artificial lens, it can be implanted substantially without stress in the lens capsule sac of an eye.

33 Claims, 6 Drawing Sheets

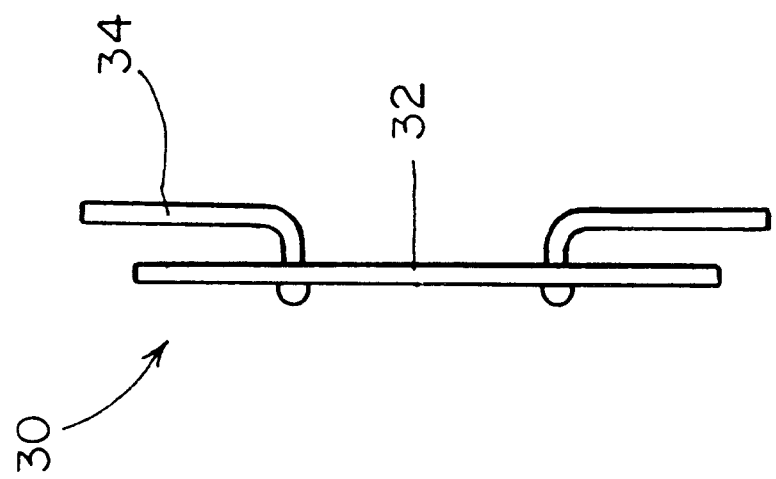
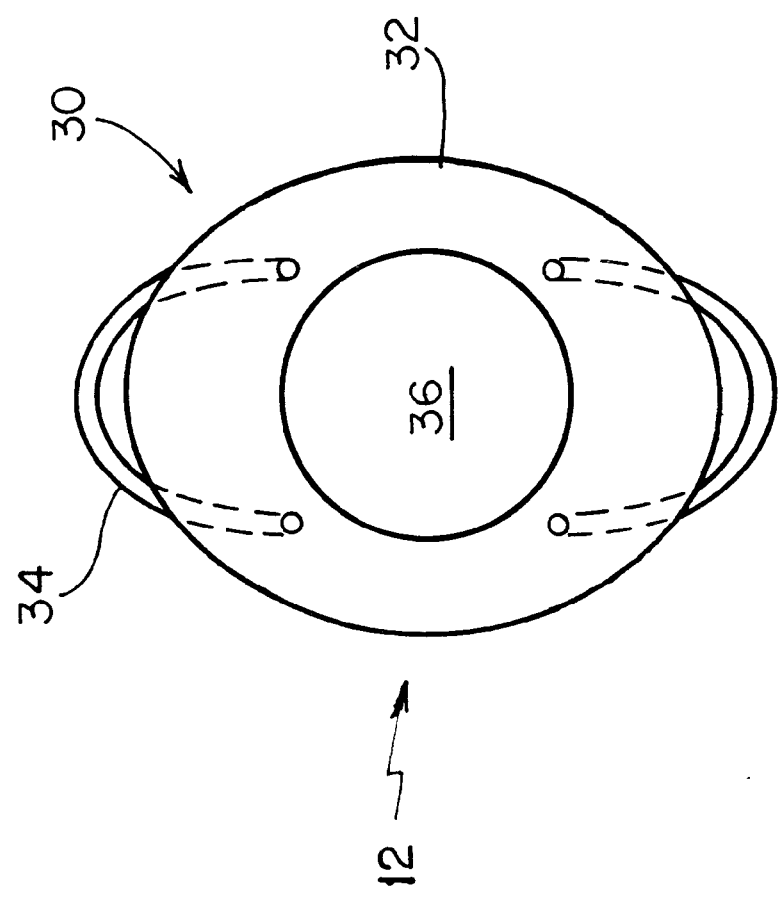

DIAPHRAGM FOR IMPLANTATION IN THE LENS CAPSULE SAC OF AN EYE

BACKGROUND OF THE INVENTION

The invention relates to a diaphragm which can be implanted in the lens capsule sac of an eye to create an artificial pupil aperture.

The state of the art in medicine is to treat gray star (cataracts) by surgical removal of the cloudy lens and to insert an artificial intraocular lens in the lens capsule sac of the eye.

To take care of iris deficiencies, there are known aniridia intraocular lenses, which are transparent within the meaning of diopter optics only in the zone of a central artificial pupil aperture and are colored at the periphery.

The use of an aniridia intraocular lens is not necessarily considered when minor defects of the iris exist. A disadvantage of this fixed combination of diaphragm with diopter optics is the generally poor or not direct availability of this prosthesis. This is due on the one hand to the complex manufacture and on the other hand to storage-related reasons, since it would be too expensive and economically unfeasible to keep a stock of all diopter strengths for non-routine cases.

Especially when complications exist, it is known that a bracing ring can be inserted as a further prosthesis in the lens capsule sac in addition to the intraocular lens, in order to brace and stabilize it and to relieve the load on the suspensory apparatus of the lens capsule. This takes place by pressure of the capsule bracing ring on the equatorial region of the capsule sac.

In the case of aniridia or of iris coloboma, the prosthetic possibility also exists of a capsule bracing ring with, for implantation in the capsule sac, one or more inwardly projecting diaphragms which are intended to leave open a central artificial pupillary aperture.

The combination of capsule bracing ring and diaphragm misses its objective, or in other words that of creating an artificial pupil of specified size, in that the "principle of action" is opposed thereto. Whereas the bracing ring exerts its bracing effect on the equatorial region of the capsule sac, the target direction of the diaphragms fixed thereto lies in the direction of the center of the capsule sac. This is the case in order to obtain an artificial pupil aperture of specified size. Because of the bracing effect, the diaphragms can become displaced behind the sclera boundaries (limbus), thus producing a too large artificial pupil aperture. As far as the pupil aperture is concerned, the result of this implant is greatly dependent on the anatomical conditions of the capsule sac and is not predictable. Thus this prosthesis does not fulfill the objective of creating a pupil aperture of specified size.

The object of the invention is to create, for implanting in the lens capsule sac of an eye, a diaphragm that is functionally decoupled from a capsule bracing ring and creates a pupil aperture of specified size.

This object is achieved with a diaphragm which, together with an artificial lens, can be implanted substantially without stress in the lens capsule sac of an eye.

The concept of this diaphragm is based on the fact that the capsule sac equator primarily exerts no force on the (compressible) diaphragm. This has the advantage that the pupil sizes defined by design remain unchanged. Further advantages of the presented concept are the uncomplicated implantability and the direct availability because of the independence from an optical system.

In a preferred embodiment, the diaphragm fits without stress in a circle of 10.5 mm to 11 mm diameter, or of up to 12 mm diameter and larger when used for very large eyes. The diaphragm extends to the circle on opposite sides.

The diaphragm can be a single diaphragm with an overlap region on one side next to a central open space and a stirrup-shaped haptic member on the other side thereof.

The haptic member is preferably C-shaped or J-shaped.

The diaphragm can also be a double diaphragm with two overlap regions on both sides of a central open space and one elastic stirrup therebeside, joining the overlap regions.

The stirrup is preferably curved inwardly in the form of a U.

The diaphragm according to the invention is preferably flat on the whole. However, it can also have one or more flat overlap regions and a haptic member angled away therefrom.

In a preferred embodiment, there can be inserted in the diaphragm a stitch which stiffens the diaphragm in the lens capsule sac after completion of implantation.

The diaphragm can be provided with one or more openings for a needle tip or a guide hook.

The diaphragm preferably comprises colored PMMA (polymethyl methacrylate) or polycarbonate.

By virtue of the invention there is created a kit of diaphragms which can be implanted one above the other with angular offset in the capsule sac, thus overlapping each other such that a central, approximately circular pupil aperture is left open.

The invention provides one kit of diaphragms each for artificial pupil apertures of 3 mm and 4 mm diameter.

In a preferred embodiment, the diaphragms of the kit can be joined with each other in the intracapsular region, and in particular can be clamped, clipped or snapped together with each other.

In a preferred embodiment, there is provided a fixing ring with a circular aperture for latching in one or more diaphragms of the said type. An exactly circular artificial pupil aperture is created by the fixing ring.

According to a further variant of the invention there is provided a circular diaphragm which comprises a foldable colored material, especially silicone or soft acrylic. For stress-free implantation in the lens capsule sac, the outside diameter of this diaphragm is 10.5 to 11 mm, or up to 12 mm and larger if used for very large eyes. The inside diameter of the diaphragm corresponds to that of the desired artificial pupil aperture, especially 3 mm or 4 mm.

The invention will be explained in more detail hereinafter on the basis of practical examples illustrated in the drawing, wherein:

FIG. 1 shows a top view of a single diaphragm;

FIG. 2 shows a top view of two single diaphragms according to FIG. 1, disposed in contact but offset 180° from each other;

FIG. 3 shows a top view of a double diaphragm;

FIG. 4 shows a top view of two double diaphragms according to FIG. 3, disposed in contact but offset 90° from each other;

FIG. 5 shows a top view of a modified single diaphragm;

FIG. 6 shows a top view of a modified double diaphragm;

FIGS. 7 to 12 show a second kit of diaphragms to create an artificial pupil aperture of 3 mm diameter and, in fact FIG. 7 shows a top view of a single diaphragm;

FIG. 8 shows a top view of two single diaphragms according to FIG. 7, disposed in contact but offset 180° from each other;

FIG. 9 shows a top view of a double diaphragm;

FIG. 10 shows a top view of a single diaphragm according to FIG. 7 and a double diaphragm according to FIG. 9, disposed in contact but offset 90° from each other;

FIG. 11 shows a top view of a fixing ring for the diaphragms; and

FIG. 12 shows a side view of the fixing ring looking in direction XII of FIG. 11.

The diaphragms 10, 12 are flat parts of colored PMMA.

The diaphragms according to FIG. 1 to FIG. 4 and FIG. 7 to FIG. 10 fit without stress in a circle 14 of 10.5 mm diameter. The diaphragms 10, 12 according to FIG. 5 and FIG. 6 fit without stress in a circle 14 of 11 mm diameter.

With the kit of diaphragms 10, 12 according to FIG. 1 to FIG. 6 there is created an artificial pupil aperture 16 of 4 mm diameter. In the kit of diaphragms according to FIG. 7 to FIG. 10 the diameter of the artificial pupil aperture 16 is 3 mm.

Figure 2:
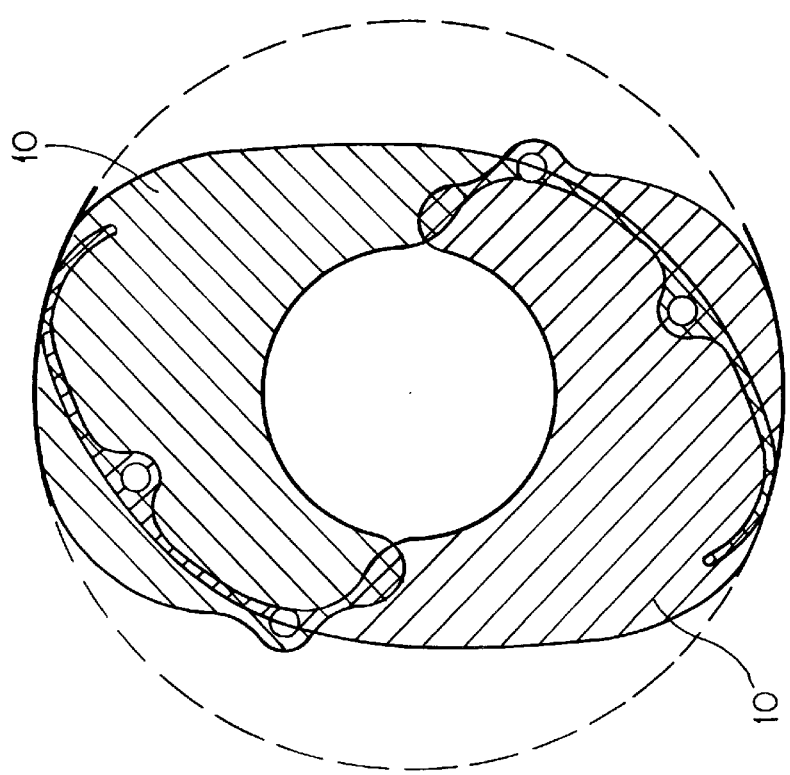
FIGS. 1 to 6 show a first kit of diaphragms for creation of an artificial pupil aperture of 4 mm diameter and, in fact.
Figure 1:
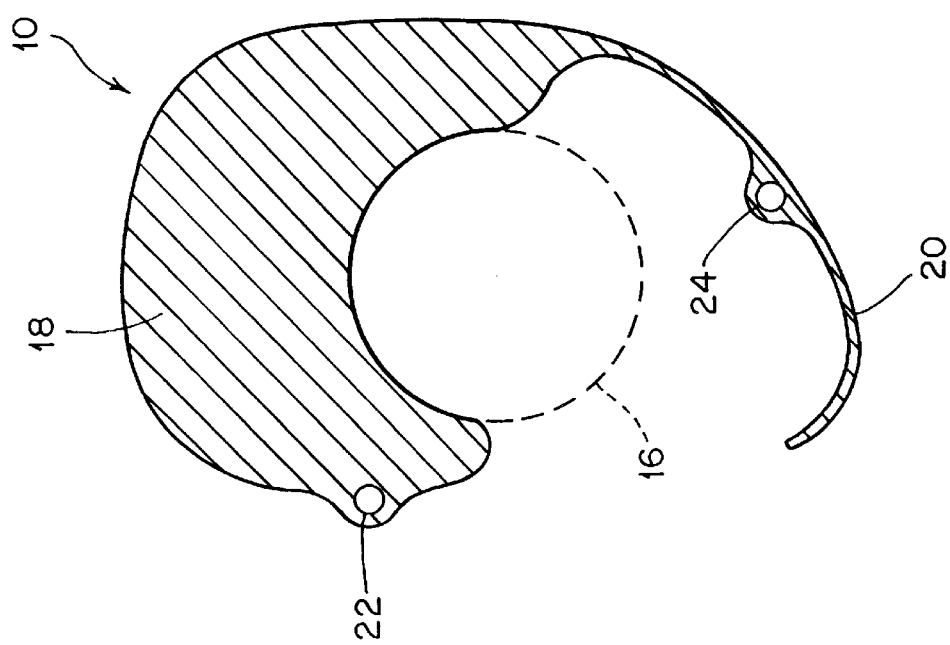

The single diaphragm 10 shown in FIGS. 1 and 2 has an overlap region 18 on one side next to the artificial pupil aperture 16. The overlap region 18 extends from the edge of the artificial pupil aperture 16 to the circle 14.

The single diaphragm 10 has a C-shaped haptic member 20, which touches the circle 14 at a position diametrically opposite the overlap region 18. The end of the haptic member 20 is bent inward away from the circle 14.

The haptic member 20 is in contact on one side with the overlap region 18. It narrows toward its end, and it leaves the artificial pupil aperture open.

At the edge of the overlap region 18 which is free of any haptic member there is provided an opening 22 for a guide hook. A further such opening 24 is disposed on the haptic member 20 close to its end in contact with the circle 14. The apertures 22, 24 are disposed approximately opposite each other.

During implantation together with an artificial lens in the capsule sac, the single diaphragm 10 is sufficient alone to cover iris colobomas (notches in the iris).

As shown in FIG. 2, a pupil can be formed by double implantation of diaphragm 10 in the capsule sac. The two single diaphragms 10 are disposed in flush contact but offset 180° from each other.

Figure 3:
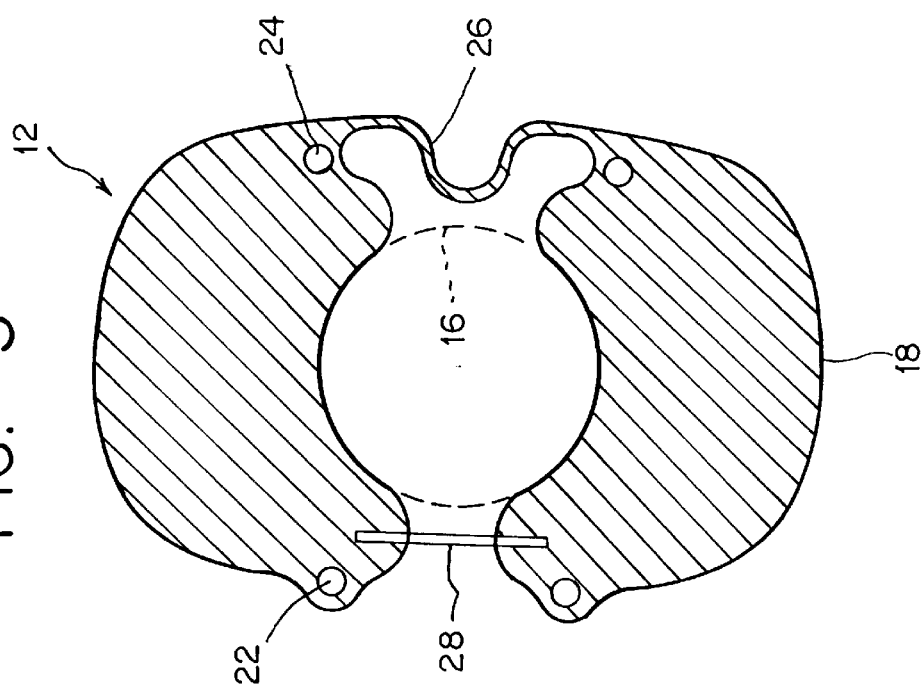

The double diaphragm 12 shown in FIG. 3 has two identically shaped overlap regions 18, which are disposed diametrically opposite each other and extend from the edge of the artificial pupil aperture 16 to the circle 14. The overlap regions 18 are joined on the one side of the artificial pupil aperture 16 by an elastic stirrup 26, which is inwardly curved in the form of a U and leaves open the artificial pupil aperture 16.

The double diaphragm 12 can be stiffened with a stitch 28, which is disposed on the side opposite the stirrup 26 and joins the overlap regions 18. The stitch 28, constructed as a straight pin, is seated in oppositely disposed blind holes of the overlapping regions 18, which holes are located in the main plane of diaphragm 12 and in the unstressed condition thereof are in alignment. The stitch 28 can be joined beforehand with one of the overlap regions 18 and in particular can even be formed integrally therewith. After implantation of the diaphragm 12 in the lens capsule sac, it is inserted into the other overlap region 18.

At their edges free of haptic members and at the stirrup attachment, the overlap regions 18 each have an opening 22, 24 for a needle tip.

During implantation together with an artificial lens in the lens capsule sac, the double diaphragm 12 is sufficient alone to cover oppositely disposed iris defects of small extent. An example is iatrogenic sphincterotomies, which had been made for treatment of narrow pupils before cataract surgery was performed.

Figure 4:
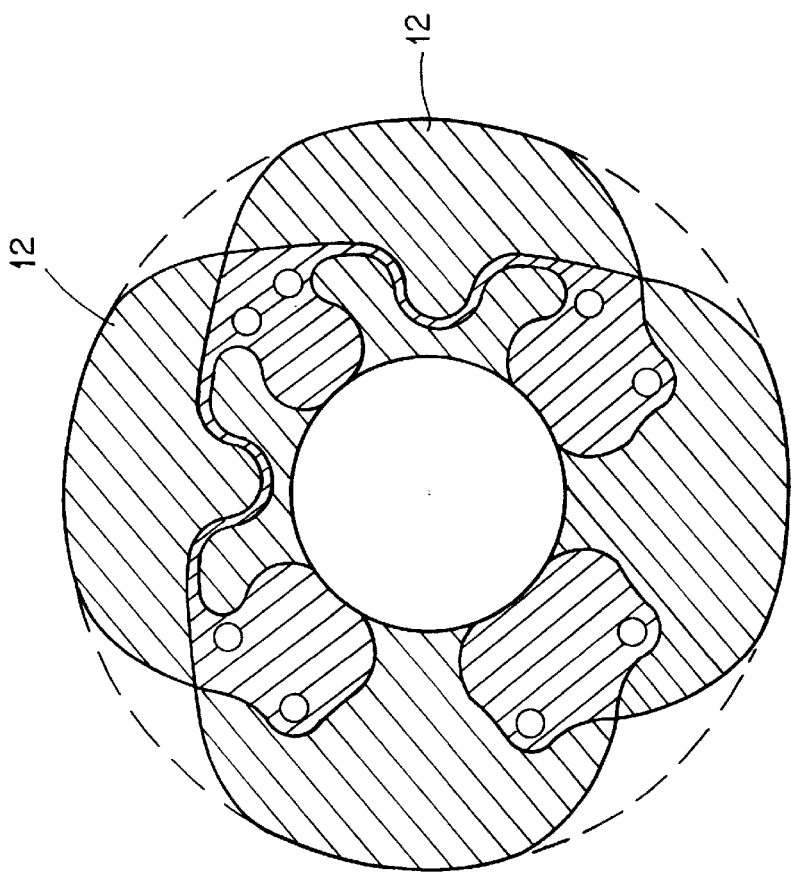

As shown in FIG. 4, an approximately circular artificial pupil aperture 16 can be created with two double diaphragms according to FIG. 3, disposed one behind the other and offset 90° relative to each other.

Figure 6:
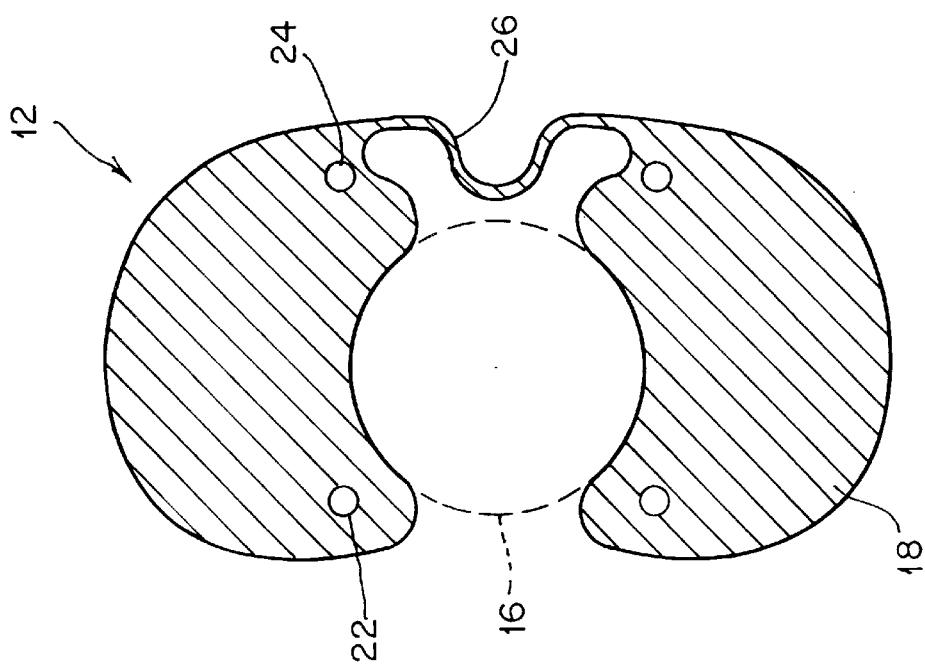
Figure 5:
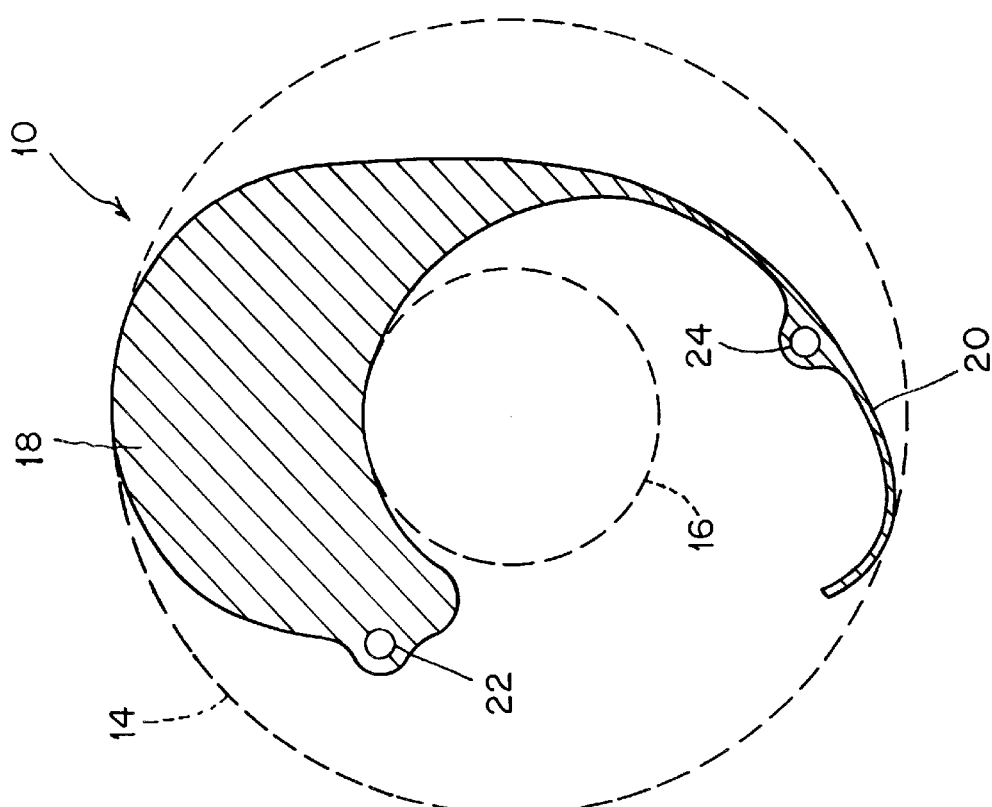
Figure 8:
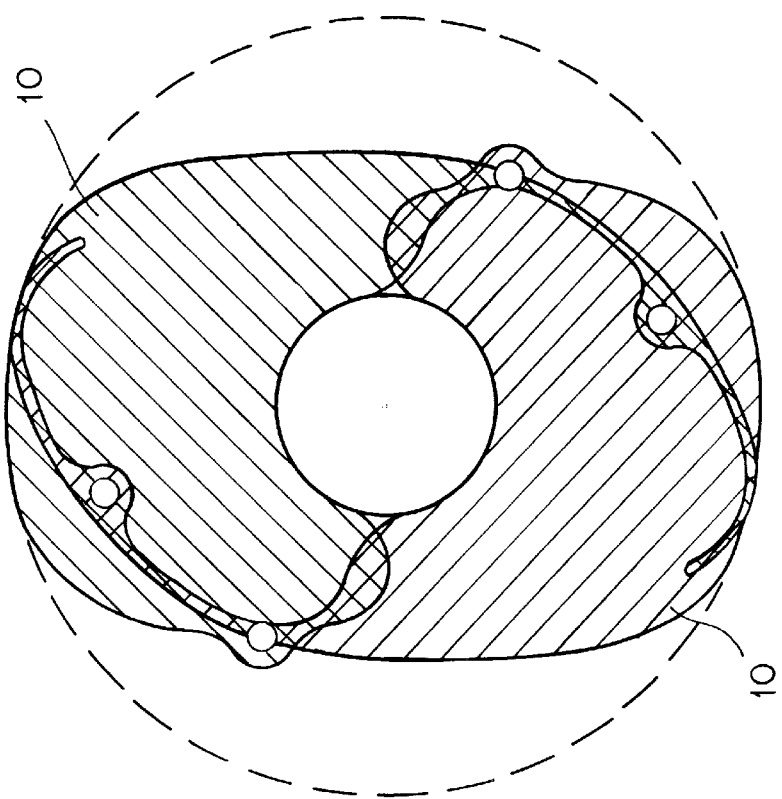
Figure 7:
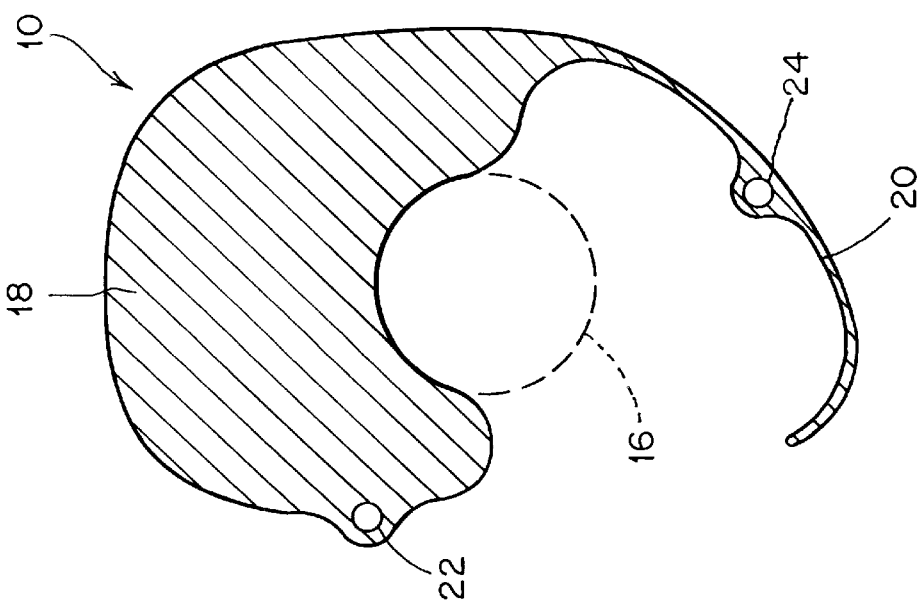

FIGS. 5 and 6 show a modified single diaphragm 10 and double diaphragm 12 with somewhat smaller overlap region 18 and somewhat larger circle 14.

In the diaphragms according to FIG. 7 to FIG. 10, the diameter of the artificial pupil aperture 16 is somewhat smaller.

Figure 10:
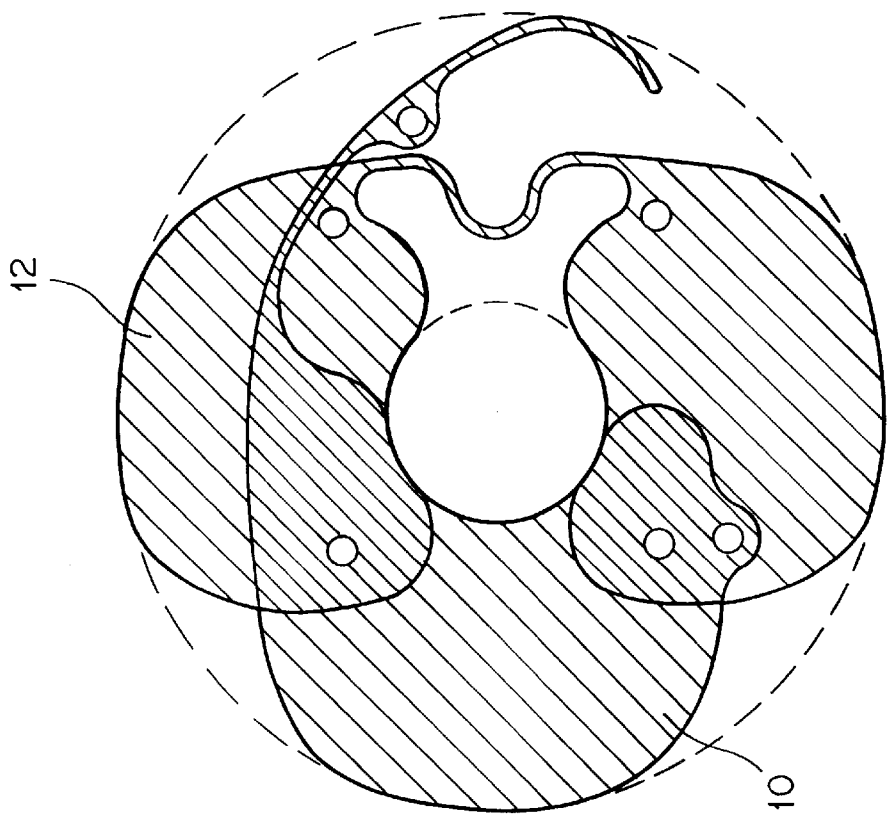
Figure 9:
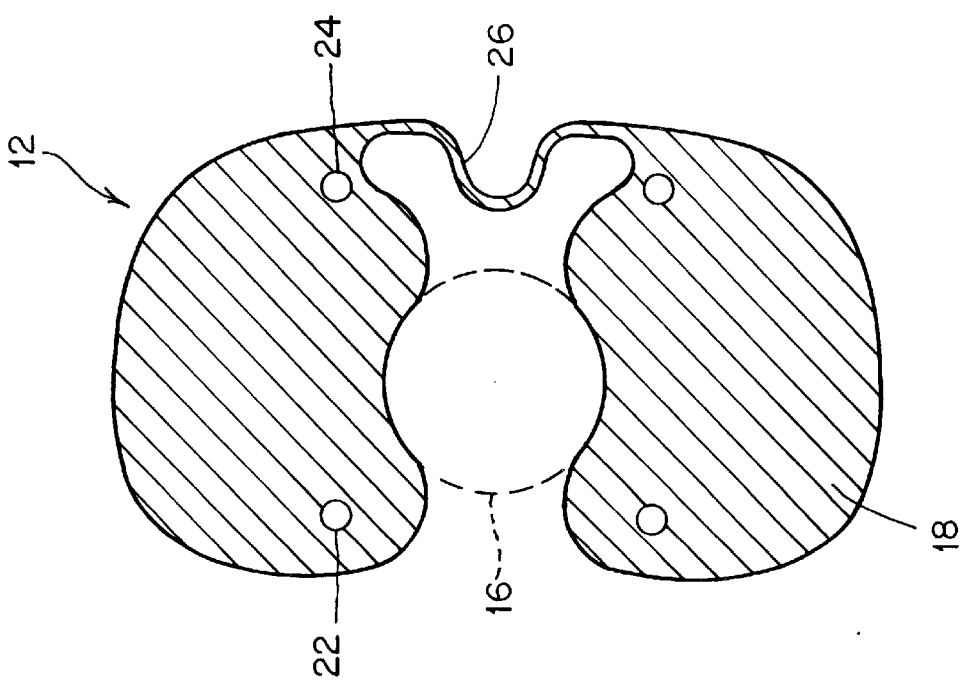

As shown in FIG. 10, the single and double diaphragms 10, 12 are also compatible with each other for implantation together in the capsule sac. The same is true for all diaphragms 10, 12 with identical size of the artificial pupil aperture 16.

FIG. 11 and FIG. 12 show a fixing ring 30 for the diaphragms 10, 12. The fixing ring 30 comprises colored PMMA. It has a flat oval annular body 32, on the broad sides of which two haptic stirrups 34 stand out perpendicular to the plane of the annulus and are bent over outward parallel thereto. The fixing ring 30 is latched by means of the haptic stirrups 34 into the diaphragms 10, 12. It has a central circular aperture 36 of 3 mm diameter.

The invention represents a concept for capsular iris diaphragms without stress. There is created a building-block system for artificial iris replacement.

The design of the building blocks for artificial iris construction is conceived such that the pupil size which exists after implantation of the building blocks in the capsule sac is predetermined by the geometry of the building blocks.

This means, assuming that the human capsule sac has an outside diameter of 10.5 mm to 11 mm, that the outside diameter of this prosthesis should not exceed 11 mm if the building blocks are to be seated without stress.

One exception in this regard is the case of myopia, in which outside diameters of 12 mm and more can be expected for the capsule sac. The building blocks can be correspondingly larger for such cases of excessive myopia.

In the case of flexible building blocks as exist in the design, a pupil size predetermined by the building-block configuration can be achieved in the capsule sac only if the capsule sac equator does not exert any stresses on the prostheses. The building-block system according to the invention satisfies these conditions, and so the predetermined pupil size is achieved in the just-operated condition.

Since capsule sacs are known to exhibit shrinkage tendencies after surgery, it cannot be ruled out that secondary stress will be exerted on the building blocks. In order that the building blocks can withstand this without deformation, it is conceivable to stiffen them in the capsule sac and/or to join them together, which can be achieved, for example, by clamping, clipping or snapping together. The building blocks can be stiffened in particular with a stitch and/or can be engaged with each other according to the plug-and-socket principle.

Because of implantation-related reasons, stiffening of the building blocks and/or joining of them together can be achieved only in the capsule sac.

The building blocks achieve their stability in the capsule sac on the one hand because of their design and on the other hand by the implantation in layers one above the other.

In each case the building blocks are preadjusted to an extent reaching the capsule sac size by means of the C-shaped haptic member or J-shaped haptic member or also by means of the two overlap regions 18 of the double diaphragm 12. Because the building blocks are disposed with their ends in the equator region of the capsule sac, the stability of their position in the just-operated and postsurgical condition is assured with simultaneous layering of the implants.

PMMA permeated with pigment (blue, green, brown) or polycarbonate is used at present as the material.

The use of other biocompatible materials is also conceivable, such as silicone or soft acrylic. A prerequisite is coloration of these materials.

Because of the fact that these materials not only are compressible but also are foldable, a circular ring with an outside diameter of approximately 10.5 mm and a pupil diameter of, for example, 3 mm or 4 mm is also worthy of consideration as the diaphragm for a capsular artificial iris insert (replacement).

| List of reference symbols | |
|---|---|
| 10 | Single diaphragm |
| 12 | Double diaphragm |
| 14 | Circle |
| 16 | Artificial pupil aperture |
| 18 | Overlap region |
| 20 | Haptic member |
| 22 | Opening |
| 24 | Opening |
| 26 | Stirrup |
| 28 | Stitch |
| 30 | Fixing ring |
| 32 | Annular body |
| 34 | Haptic stirrup |
| 36 | Aperture |

What is claimed is:

1. A single diaphragm configured to be implanted substantially without stress in the lens capsule sac of an eye, together with an artificial lens, in order to create an artificial pupil aperture comprising an overlap region on one side next to a central open space and a stirrup-shaped haptic member on the other side thereof.

2. A single diaphragm according to claim 1, wherein said diaphragm fits without stress in a circle of 10.5 mm to 11 mm diameter, or of up to 12 mm diameter and larger when used for very large eyes, and extends to the circle on opposite sides.

3. A single diaphragm according to claim 1, wherein said haptic member is C-shaped or J-shaped.

4. A single diaphragm according to claim 1, wherein said diaphragm is flat.

5. A single diaphragm according to claim 1, wherein said diaphragm has at least one flat overlap region and said haptic member is angled away therefrom.

6. A single diaphragm according to claim 1, additionally including a stitch inserted in said diaphragm to stiffen the same.

7. A single diaphragm according to claim 1, additionally including at least one opening for a needle tip or a guide hook.

8. A single diaphragm according to claim 1, wherein said diaphragm is made of a material selected from the group consisting of colored polymethyl methacrylate and polycarbonate.

9. A single diaphragm according to claim 1, additionally including a fixing ring having a circular aperture for latching said diaphragm.

10. A single diaphragm according to claim 1, wherein said diaphragm comprises a foldable colored material and is circular.

11. A single diaphragm according to claim 1, wherein said diaphragm is made of silicone.

12. A single diaphragm according to claim 1, wherein said diaphragm is made of soft acrylic.

13. A kit comprising a plurality of diaphragms configured to be implanted substantially without stress in the lens capsule sac of an eye, together with an artificial lens, in order to create an artificial pupil aperture comprising an overlap region on one side next to a central open space and a stirrup-shaped haptic member on the other side thereof, wherein said diaphragms can be implanted one above the other with angular offset in the capsule sac, thus overlapping each other such that a central, approximately circular artificial pupil aperture is left open.

14. A kit according to claim 13, wherein said diaphragms are dimensioned to define an artificial pupil aperture of 3 mm diameter.

15. A kit according to claim 13, wherein said diaphragms are dimensioned to define an artificial pupil aperture of 4 mm diameter.

16. A kit according to claim 13, wherein said diaphragms are joined to each other in the intracapsular region.

17. A double diaphragm configured to be implanted substantially without stress in the lens capsule sac of an eye, together with an artificial lens, in order to create an artificial pupil aperture comprising two overlap regions disposed opposite each other on both sides of a central open space and with one elastic stirrup therebeside, joining said overlap regions.

18. A double diaphragm according to claims 17, wherein said diaphragms fit without stress in a circle of 10.5 mm to 11 mm diameter, or of up to 12 mm diameter and larger when used for very large eyes, and extends to the circle on opposite sides.

19. A double diaphragm according to claim 17, wherein said stirrup is curved inwardly in the form of a U.

20. A double diaphragm according to claim 17, wherein said diaphragm is flat.

21. A double diaphragm according to claim 17, wherein said diaphragm has at least one flat overlap region and a haptic member angled away therefrom.

22. A double diaphragm according to claim 17, additionally including a stitch inserted in said diaphragms to stiffen the same.

23. A double diaphragm according to claim 17, additionally including at least one opening for a needle tip or a guide hook.

24. A double diaphragm according to claim 17, wherein said diaphragm is made of a material selected from the group consisting of colored polymethyl methacrylate and polycarbonate.

25. A double diaphragm according to claim 17, additionally including a fixing ring with a circular aperture for latching said diaphragms.

26. A double diaphragm according to claim 17, wherein said diaphragms comprise a foldable colored material and are circular.

27. A double diaphragm according to claim 17, wherein said diaphragms are made of silicone.

28. A double diaphragm according to claim 17, wherein said diaphragms are made of soft acrylic.

29. A kit comprising a plurality of double diaphragms configured to be implanted substantially without stress in the lens capsule sac of an eye, together with an artificial lens, in order to create an artificial pupil aperture comprising two overlap regions disposed opposite each other on both sides of a central open space and with one elastic stirrup therebeside, joining said overlap regions, wherein said diaphragms can be implanted one above the other with angular offset in the capsule sac, thus overlapping each other such that a central, approximately circular artificial pupil aperture is left open.

30. A kit according to claim 29, wherein said diaphragms are dimensioned to define an artificial pupil aperture of 3 mm diameter.

31. A kit according to claim 29, wherein said diaphragms are dimensioned to define an artificial pupil aperture of 4 mm diameter.

32. A kit according to claim 29, wherein said diaphragms are joined to each other in the intracapsular region.

33. A kit according to claim 13 wherein said plurality of diaphragms includes at least one single diaphragm and at least one double diaphragm, the latter of which is configured to be implanted substantially without stress in the lens capsule sac of an eye, together with an artificial lens, in order to create an artificial pupil aperture comprising two overlap regions disposed opposite each other on both sides of a central open space and with one elastic stirrup therebeside, joining said overlap regions, wherein said diaphragms can be implanted one above the other with angular offset in the capsule sac, thus overlapping each other such that a central, approximately circular artificial pupil aperture is left open.

* * * * *